United States Patent [19]

Shutske

[11] Patent Number: 4,658,029

[45] Date of Patent: Apr. 14, 1987

[54] 1-HPYRAZOLO[3,4-B]PYRIDINES

[75] Inventor: Gregory M. Shutske, Somerset, N.J.

[73] Assignee: Hoechst-Roussel Pharmaceuticals Inc., Somerville, N.J.

[21] Appl. No.: 896,919

[22] Filed: Aug. 15, 1986

Related U.S. Application Data

[62] Division of Ser. No. 812,590, Dec. 23, 1985, Pat. No. 4,622,326.

[51] Int. Cl.$^4$ ............................................. C07D 471/04
[52] U.S. Cl. ...................................... 546/119; 546/120
[58] Field of Search ................................ 546/120, 119

[56] References Cited

FOREIGN PATENT DOCUMENTS 6100783  1/1980  Japan ................................. 546/119

Primary Examiner—Henry R. Jiles
Assistant Examiner—J. Richter
Attorney, Agent, or Firm—Tatsuya Ikeda

[57] ABSTRACT

This invention claims compounds having the formulae

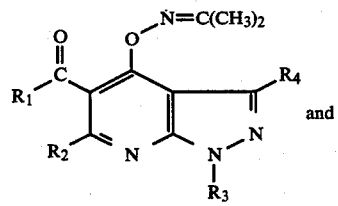

and

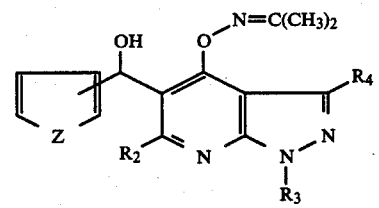

where $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; $R_4$ is hydrogen or loweralkyl; and Z is O, S, $NR_5$ or CH=N, $R_5$ being loweralkyl, phenylloweralkyl or benzensulfonyl. These compounds are useful as intermediates for synthesizing 6H-isoxazolo[5,4-d]pyrazolo[3,4-b]pyridines which in turn are useful as analgesic and hypotensive agents.

14 Claims, No Drawings

1-HPYRAZOLO[3,4-B]PYRIDINES

This is a division of application Ser. No. 812,590 filed Dec. 23, 1985, now U.S. Pat. No. 4,622,326.

This invention relates to compounds having the formula

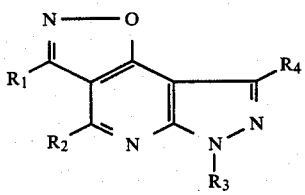

wherein $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl; or a pharmaceutically acceptable acid addition salt thereof, which are useful for alleviating pain and lowering blood pressure, methods for synthesizing them, and pharmaceutical compositions comprising an effective amount of such a compound.

This invention also relates to compounds of formulas (II) and (III) below

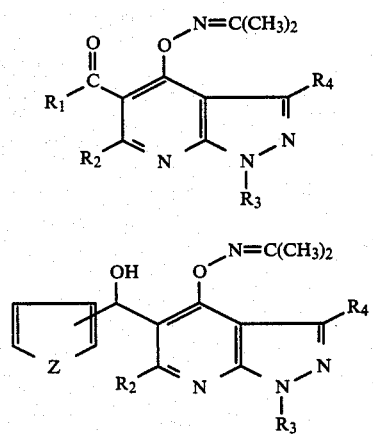

where $R_1$ through $R_4$ are as defined above and Z is O, S, $NR_5$ or CH=N, $R_5$ being loweralkyl, phenylloweralkyl or benzenesulfonyl, which are useful as intermediate compounds for synthesizing the compounds of Formula I and methods for synthesizing them.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl includes methyl, ethyl, n-propyl, iso-propyl, n-butyl, iso-butyl, sec-butyl, t-butyl and straight- and branched-chain pentyl and hexyl.

Unless otherwise states or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term cycloalkyl shall mean a cycloalkyl group of 3 to 7 carbon atoms.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently a loweralkyl group, loweralkoxy group, hydroxy group, trifluoromethyl group, chlorine or fluorine, with the proviso that the aryl group shall not have chlorine or fluorine at the ortho position.

Unless otherwise stated or indicated, the term heteroaryl group shall mean a group having the formula

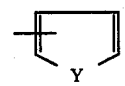

where Y is O, S, $NR_6$ or CH=N, $R_6$ being hydrogen, loweralkyl or phenylloweralkyl, and it shall include all the positional isomers. Thus, for instance, the term shall include both 2-furyl and 3-furyl.

The compounds of this invention are prepared by utilizing one or more of the steps described below.

Throughout the description of the synthetic steps, the notations $R_1$, $R_2$, $R_3$, $R_4$, $R_5$, $R_6$, Y and Z shall have the respective meanings given above unless otherwise stated or indicted.

Preferred synthetic steps used for synthesizing the compounds of this invention are schematically shown in FIG. 1. It should be understood, however, that FIG. 1 is merely a schematic representation presented for the purpose of illustration and it should not be construed too narrowly.

For details of the reaction steps used for preparing compound V depicted in FIG. 1, the reader is referred to H. Hoehn, Th. Denzel and W. Jansen, J. Heterocyclic Chem. 9, 235 (1972), except that in this invention a low temperature (about −75° C. to −40° C.) Grignard reaction was used for the last step as shown in FIG. 1, whereas Hoehn et al. used a cadmium-Grignard reagent at a higher temperature.

STEP A

Compound V where $R_1$ is not H or heteroaryl is reacted with acetone oxime salt $(CH_3)_2$=N—O⁻K⁺ to afford compound IIA as shown in FIG. 1. Typically, this reaction is conducted by first preparing the potassium salt of acetone oxime anion by reacting acetone oxime with potassium tertiary-butoxide for instance in a suitable solvent such as anhydrous tetrahydrofuran (THF) at room temperature and thereafter adding to the mixture a solution of compound V in a suitable solvent such as THF and stirring the resultant mixture at room temperature. Sodium salt of acetone oxime anion may also be used.

STEP B

Compound IIa where $R_1$ is not hydrogen or heteroacryl is converted to compound Ia in the presence of $H_3O^+$ as shown in FIG. 1. Typically this acid-catalyzed transoximation reaction is conducted by heating a mixture comprising compound IIa and a suitable medium such as water and ethanol as well as a protonic acid such as HCl. Reflux is preferred.

As an alternative to STEPS A and B, the following two steps may also be used.

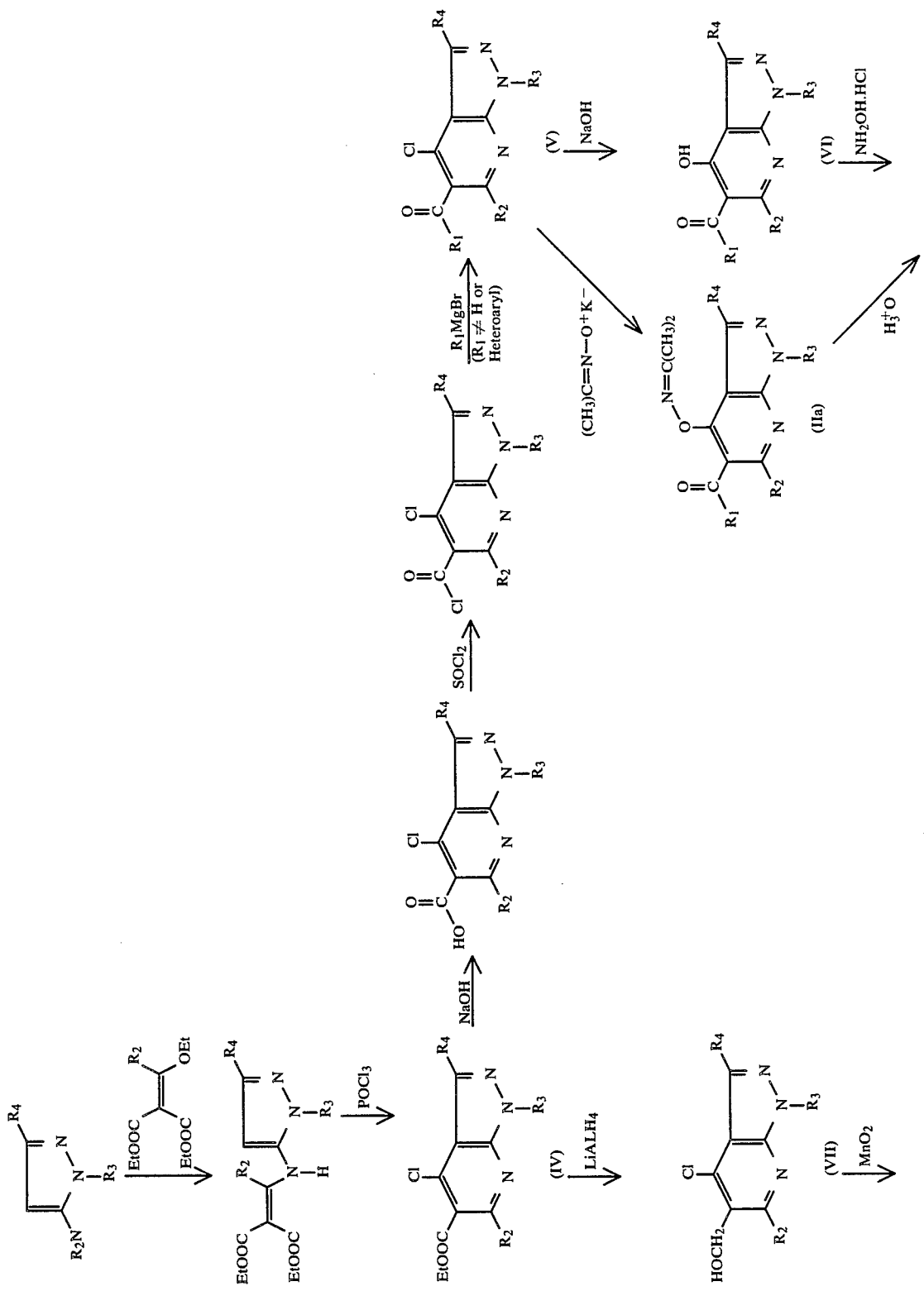

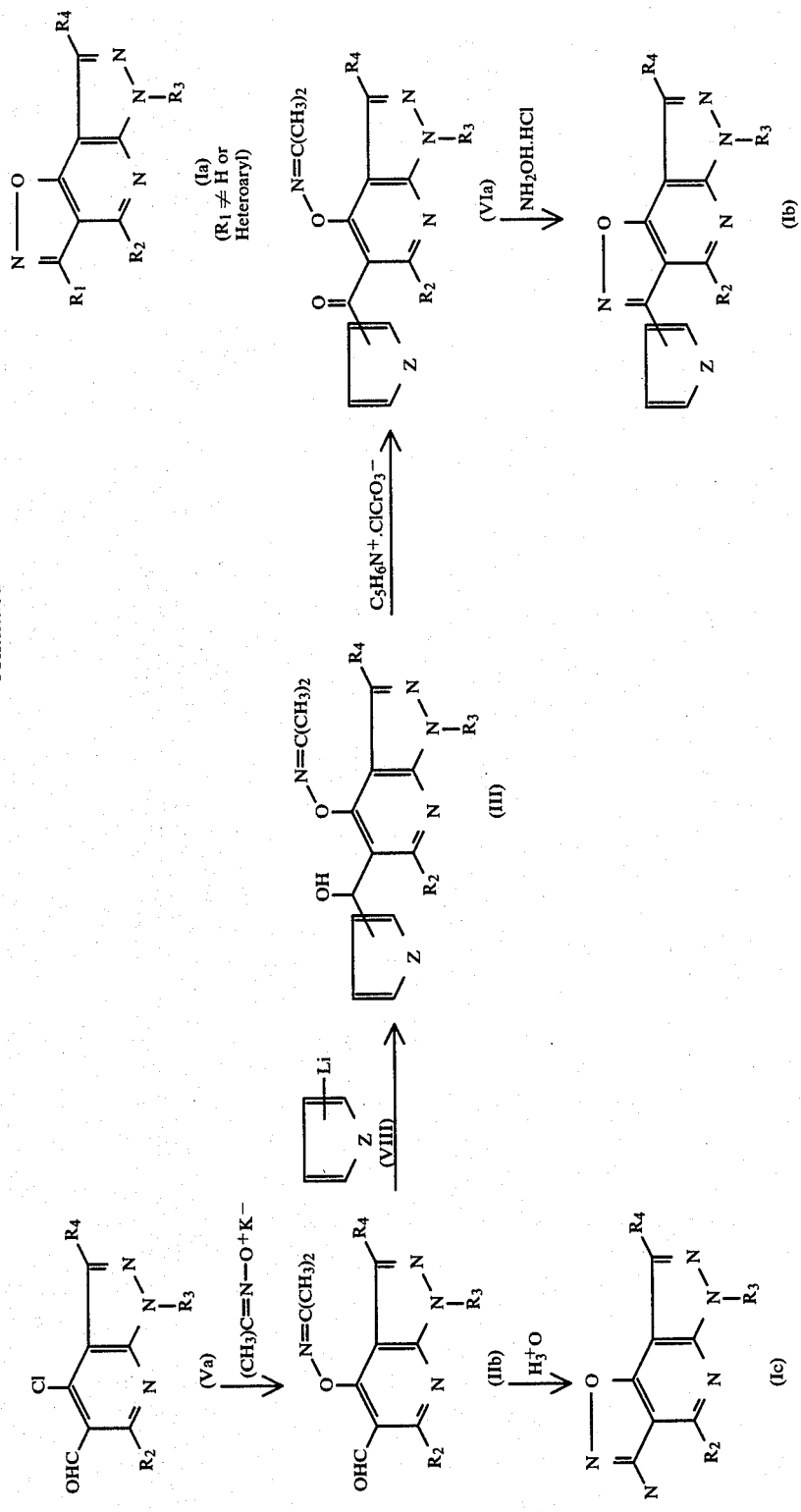

STEP C

Compound V where $R_1$ is not hydrogen or heteroaryl is hydrolyzed to compound VI as shown in FIG. 1. Said hydrolysis is conducted in a suitable medium such as a mixture comprising water and dimethylsulfoxide and in the presence of an alkaline catalyst such as NaOH. A typical reaction temperatue is about 50° to 100° C.

STEP D

Compound VI where $R_1$ is not hydrogen or heteroaryl is reacted with hydroxylamine to obtain compound Ia as shown in FIG. 1. This cyclization reaction is typically conducted by relfuxing a mixture comprising compound VI, hydroxylamine hydrochloride and a suitable solvent such as pyridine.

STEP E

Compound IV is reduced with $LiAlH_4$ to obtain compound VII as shown in FIG. 1. Typically said reduction is conducted in a suitable medium such as anhydrous THF, diethyl ether or the like at a temperature of about 0°–30° C.

STEP F

Compound VII is oxidized to compound Va with manganese dioxide as shown in FIG. 1. Typically said oxidation is conducted in a suitable medium such as benzene or toluene at a temperature of about 80°–120° C.

STEP G

Compound Va is reacted with acetone oxime salt $(CH_3)_2C=N-O^-K^+$ to obtain compound IIb as shown in FIG. 1. This step is conducted in substantially the same manner as STEP A above.

STEP H

Compound IIb is reacted with heteroaryl lithium of formula VIII where Z is O, S, $NR_5$ or CH=N, $R_5$ being loweralkyl, phenylloweralkyl or benzenesulfonyl as mentioned above to obtain compound III as shown in FIG. 1. When Z is CH=N, the organolithium compound VIII is prepared from n-butyl lithium and a bromo compound of the formula

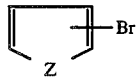

in a suitable solvent such as anhydrous ether at a temperature of between about −70° C. and −50° C. When Z is O, S or $NR_6$, compound VIII is prepared from n-butyl lithium and a compound of the formula

in a suitable solvent such as anhydrous ether at a temperature of between about −20° C. and +40° C. Thereafter the solution of compound VIII prepared above is added to the solution a solution of compound IIb in a suitable solvent such as anhydrous THF and the reaction mixture is stirred at a temperature between about −10° C. and 10° C.

When Z is benzenesulfonyl substituted nitrogen, 1-benzenesulfonylpyrrole which is used for preparing compound VIII can readily be prepared from pyrrolyl anion and benzenesulfonyl chloride by routine procedure.

STEP I

Compound III is oxidized to compound VIa with pyridinium chlorochromate to obtain compound VIa as shown in FIG. 1. This oxidation is typically conducted by adding pyridinium chlorochromate to a solution of compound VIa in a suitable solvent such as dichloromethane and stirring the mixture at a temperature of about 10°–50° C.

STEP J

Compound VIa is reacted with hydroxylamine to obtain compound Ib as shown in FIG. 1. This step is conducted in substantially the same manner as STEP D.

STEP K

Although not indicated in FIG. 1, when the group Z is benzenesulfonyl substituted nitrogen in formula Ib, the benzenesulfonyl group can be converted to hydrogen by hydrolyzing the compound Ib. Said hydrolysis is conducted typically in the presence of NaOH or KOH and a suitable medium such as lower aliphatic alcohol at a temperature of about 80°–120° C.

As a result of STEP J and STEP K, compound I where $R_1$ is a heteroaryl group of the formula

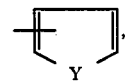

where Y is O, S, $NR_6$ or CH=N, $R_6$ being hydrogen, loweralkyl or phenylloweralyl are obtained.

STEP L

Compound IIb is hydrolyzed to obtain compound Ic as shown in FIG. 1. This step is conducted in substantially the same manner as STEP B above.

STEP M

Where the group $R_1$ in the target compound I is a phenyl group substituted with one or more hydroxy groups, said compound is prepared by first synthesizing the corresponding methoxy substituted compound according to the reaction scheme described above and then converting the methoxy group or groups to hydroxy group or groups by cleavage reaction. Said cleavage reaction is typically conducted by refluxing a mixture comprising the methoxy compound, boron tribormide and a suitable solvent such as 1,2-dichloroethane and thereafter pouring the reaction mixture into ice water.

The 6H-isoxazolo[5,4-d]pyrazolo[3,4-d]pyridines of formula I of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mmHg), are given in Table I.

TABLE I

| ANTIHYPERTENSIVE ACTIVITY | |
|---|---|
| Compound | Antihypertensive SHR mmHg at 50 mg/kg, PO |
| 3-(4-Chlorophenyl)-6-ethyl-6H—isoxazolo[5,4-d]pyrazolo[3,4-b]-pyridine | 62 |

TABLE I-continued
ANTIHYPERTENSIVE ACTIVITY

| Compound | Antihypertensive SHR mmHg at 50 mg/kg, PO |
|---|---|
| 6-Ethyl-3-(4-methoxyphenyl)-6H—isoxazolo[5,4-d]pyrazolo[3,4-b]pyridine | 31 |
| 6-Ethyl-3-(3-tolyl)-6H—isoxazolo[5,4-d]pyrazolo[3,4-b]pyridine | 33 |
| (Prior Art Compound) alpha-Methyldopa | 40 |

Compounds I of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 2 shows a result of the test of the analgesic activities of some of the compounds of this invention.

TABLE 2
ANALGESIC ACTIVITY
(Phenylquinone Writhing)

| Compound | Analgesic PQW, % decrease at 20 mg/kg, SC |
|---|---|
| 6-Ethyl-3-tolyl-6H—isoxazolo[5,4-d]pyrazolo[3,4-b]pyridine | 48 |
| 6-Ethyl-3-(4-fluorophenyl)-6H—isoxazolo[5,4-d]pyrazolo[3,4-b]pyridine | 31 |
| 6-Ethyl-3-(3-fluorophenyl)-6H—isoxazolo[5,4-d]pyrazolo[3,4-b]pyridine | 55 |
| 6-Ethyl-3-(3-hydroxyphenyl)-6H—isoxazolo[5,4-d]pyrazolo[3,4-b]pyridine | 48 |
| 6-Ethyl-3-(2-pyridyl)-6H—isoxazolo[5,4-d]pyrazolo[3,4-b]pyridine | 42 |
| (Prior Art Compound) Propoxyphene | $ED_{50}$ = 3.9 mg/kg, s.c. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution of suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral multiple dose vials made of glass or plastic.

Examples of the compounds of this invention include:
6-Ethyl-3-phenyl-6H-isoxazolo[5,4-d]pyrazolo[3,4-b]pyridine;
6-Ethyl-3-(3-tolyl)-6H-isoxazolo[5,4-d]pyrazolo[3,4-b]pyridine;
6-Ethyl-3-(4-tolyl)-6H-isoxazolo[5,4-d]pyrazolo[3,4-b]pyridine;
6-Ethyl-3-(3-fluorophenyl)-6H-isoxazolo[5,4-d]pyrazolo[3,4-b]pyridine;
6-Ethyl-3-(4-fluorophenyl)-6H-isoxazolo[5,4-d]pyrazolo[3,4-b]pyridine;
3-(3-Chlorophenyl)-6-ethyl-6H-isoxazolo[5,4-d]pyrazolo[3,4-b]pyridine;
3-(4-Chlorophenyl)-6-ethyl-6H-isoxazolo[5,4-d]pyrazolo[3,4-b]pyridine;
6-Ethyl-3-(3-methoxyphenyl)-6H-isoxazolo[5,4-d]pyrazolo[3,4-b]pyridine;
6-Ethyl-3-(4-methoxyphenyl)-6H-isoxazolo[5,4-d]pyrazolo[3,4-b]pyridine;

6-Ethyl-3-(3-hydroxyphenyl)-6H-isoxazolo[5,4-d]pyrazolo[3,4-b]pyridine;

6-Ethyl-3-(2-pyridyl)-6H-isoxazolo[5,4-d]pyrazolo[3,4-b]pyridine;

5-Benzoyl-1-ethyl-4-isopropylidenaminooxy-1H-pyrazolo[3,4-b]pyridine;

5-(4-Chlorobenzoyl)-1-ethyl-4-isopropylidenaminooxy-1H-pyrazolo[3,4-b]pyridine;

(1-Ethyl-4-isopropylidenaminooxy-1H-pyrazolo[3,4-b]pyridin-5-yl)(2-pyridyl)carbinol; and 1-Ethyl-4-isopropylidenaminooxy-1H-pyrazolo[3,4-b]pyridine-5-carboxaldehyde.

EXAMPLE 1

6-Ethyl-3-phenyl-6H-isoxazolo[5,4-d]pyrazolo[3,4-b]pyridine

5-Benzoyl-1-ethyl-4-isopropylideneaminooxy-1H-pyrazolo [3,4-b]pyridine (2.50 g) was refluxed for 2 hours in a mixture prepared from 100 ml of 5% hydrochloric acid and 15 ml of ethanol. The reaction mixture was then extracted into ether and washed consecutively with 5% sodium hydroxide solution and water. Evaporation of the organic phase gave 1.65 g of product. An analytical sample recrystallized from ethyl acetate/methanol had mp 151°–153° C.

ANALYSIS:
| | | | |
|---|---|---|---|
| Calculated for $C_{15}H_{12}N_4O$: | 68.17% C | 4.58% H | 21.20% N |
| Found: | 68.23% C | 4.65% H | 21.25% N |

EXAMPLE 2

6-Ethyl-3-(3-tolyl)-6H-isoxazolo[5,4-d]pyrazolo[3,4-b]pyridine

1-Ethyl-4-hydroxy-5-(3-methylbenzoyl)-1H-pyrazolo[3,4-b]pyridine (4.25 g) was refluxed overnight in 75 ml of pyridine containing 4.5 g of hydroxylamine hydrochloride. The pyridine was then removed under reduced pressure and the residue triturated with 5% hydrochloric acid. The product was then filtered off and recrystallized from methanol to give 2.63 g of analytically pure product, mp 122°–123° C.

ANALYSIS:
| | | | |
|---|---|---|---|
| Calculated for $C_{16}H_{15}N_4O$: | 69.05% C | 5.07% H | 20.13% N |
| Found: | 68.78% C | 5.19% H | 20.24% N |

EXAMPLE 3

6-Ethyl-3-(4-tolyl)-5H-isoxazolo[3,4-d]pyrazolo[3,4-b]pyridine

1-Ethyl-4-hydroxy-5-(4-methylbenzoyl)-1H-pyrazolo[3,4-b]pyridine (1.45 g) was refluxed overnight in 20 ml of pyridine containing 3.0 g of hydroxylamine hydrochloride. The pyridine was then evaporated and the residue triturated with 5% hydrochloric acid and then washed with methanol. In this manner 1.26 g of product was obtained, mp 173°–175° C. An analytical sample was recrystallized from dichloromethane/hexane and the melting point was unchanged.

ANALYSIS:
| | | | |
|---|---|---|---|
| Calculated for $C_{16}H_{14}N_4O$: | 69.05% C | 5.07% H | 20.13% N |
| Found: | 68.88% C | 5.14% H | 30.23% N |

EXAMPLE 4

6-Ethyl-3-(3-fluorophenyl)-6H-isoxazolo[5,4-d]pyrazolo[3,4-b]pyridine

1-Ethyl-5-(3-fluorobenzoyl)-4-hydroxy-1H-pyrazolo[3,4-b]pyridine (2.85 g) was refluxed overnight in 50 ml of pyridine containing 3.0 g of hydroxylamine hydrochloride. The pyridine was evaporated and the residue triturated with 5% hydrochloric acid. The product thus obtained was filtered off and recrystallized from methanol to give 2.21 g of analytically pure product, mp 136°–137° C.

ANALYSIS:
| | | | |
|---|---|---|---|
| Calculated for $C_{15}H_{11}FN_4O$: | 63.82% C | 3.93% H | 19.85% N |
| Found: | 63.92% C | 4.05% H | 19.90% N |

EXAMPLE 5

6-Ethyl-3-(4-fluorophenyl)-6H-isoxazolo[5,4-d]pyrazolo[3,4-b]pyridine

1-Ethyl-5-(4-fluorobenzoyl)-4-hydroxy-1H-pyrazolo[3,4-b]pyridine (3.35 g) was refluxed overnight in 75 ml of pyridine containing 4.0 g of hydroxylamine hydrochloride. The solvent was then evaporated and the residue triturated with 5% hydrochloric acid. The product thus obtained was washed with methanol and then chromatographed over silica gel (5% methanol/dichloromethane) to remove a trace of fluorescent impurity. After recrystallization from ethyl acetate/hexane, 2.83 g of product was obtained, mp 175°–176° C.

ANALYSIS:
| | | | |
|---|---|---|---|
| Calculated for $C_{15}H_{11}FN_4O$: | 63.82% C | 3.93% H | 19.85% N |
| Found: | 63.80% C | 3.93% H | 20.10% N |

EXAMPLE 6

3-(3-Chlorophenyl)-6-ethyl-6H-isoxazolo[5,4-d]pyrazolo[3,4-b]pyridine 5-(3-Chlorobenzoyl)-1-ethyl-4-hydroxy-1H-pyrazolo[3,4-b]pyridine (4.25 g) was refluxed overnight in 100 ml of pyridine containing 4.5 g of hydroxylamine hydrochloride. The reaction mixture was then evaporated and the residue triturated with 5% hydrochloric acid. The resulting product was then filtered off and washed with methanol. Recrystallization from ethyl acetate gave analytically pure product (1.91 g), mp 178°–179° C.

ANALYSIS:
| | | | |
|---|---|---|---|
| Calculated for $C_{15}H_{11}ClN_4O$: | 60.31% C | 3.71% H | 18.76% N |
| Found: | 60.10% C | 3.68% H | 18.89% N |

EXAMPLE 7

3-(4-Chlorophenyl)-6-ethyl-6H-isoxazolo[5,4-d]pyrazolo[3,4-b]pyridine 5-(4-chlorobenzoyl)-1-ethyl-4-isopropylideneaminooxy-1H-pyrazolo-[3,4-b]pyridine (3.54 g) was refluxed for 2 hours in 75 ml of 2:1 5% hydrochloric acid/ethanol. The reaction mixture was distributed between water and ether and then the ether layer was washed with 5% sodium hydroxide. Evaporation of the ether gave 1.30 g of product. An analytical sample was recrystallized from hexane which had mp 195°–197° C.

ANALYSIS:

| | | | |
|---|---|---|---|
| Calculated for $C_{15}H_{11}ClN_4O$: | 60.31% C | 3.71% H | 18.76% N |
| Found: | 60.68% C | 3.83% H | 18.64% N |

EXAMPLE 8

6-Ethyl-3-(3-methoxyphenyl)-6H-isoxazolo[5,4-d]pyrazolo[3,4-b]pyridine

1-Ethyl-4-hydroxy-5-(3-methoxybenzoyl)-1H-pyrazolo-[3,4-b]pyridine was refluxed overnight in 75 ml of pyridine containing 7.0 g of hydroxylamine hydrochloride. The pyridine was evaporated and the residue triturated with 5% hydrochloric acid. The product thus obtained was recrystallized from methanol to give 5.94 g, mp 130°–131° C.

ANALYSIS:

| | | | |
|---|---|---|---|
| Calculated for $C_{16}H_{14}N_4O_2$: | 65.29% C | 4.79% H | 19.04% N |
| Found: | 65.16% C | 4.75% H | 19.15% N |

EXAMPLE 9

6-Ethyl-3-(4-methoxyphenyl)-6H-isoxazolo[5,4-d]pyrazolo[3,4-b]pyridine

1-Ethyl-4-hydroxy-5-(4-methoxybenzoyl)-1H-pyrazolo[3,4-b]pyridine (3.60 g) was refluxed overnight in 30 ml of pyridine containing 4.0 g of hydroxylamine hydrochloride. At the end of this time the pyridine was evaporated and the residue triturated with 5% hydrochloric acid. The product obtained in this manner was chromatographed silica gel (5% methanol/dichloromethane) to remove a fluorescent impurity. Combination of the appropriate fractions and recrystallization from dichloromethane/hexane gave 2.95 g of pure product, mp 156°–157° C.

ANALYSIS:

| | | | |
|---|---|---|---|
| Calculated for $C_{16}H_{14}N_4O_2$: | 65.29% C | 4.79% H | 19.04% N |
| Found: | | 64.87% C | 4.84% H | 19.08% N |

EXAMPLE 10

6-Ethyl-3-(3-hydroxyphenyl)-6H-isoxazolo[5,4-d]pyrazolo[3,4-b]pyridine

6-Ethyl-3-(3-methoxyphenyl)-6H-isoxazolo[5,4-d]pyrazolo[3,4-d]pyridine (3.84 g) was dissolved in 75 ml of 1,2-dichloroethane and to this was added 7.5 ml of $BBr_3$ (19.9 g). The reaction mixture was then refluxed for 3 hours, at which time thin layer chromatography showed complete reaction. The reaction mixture was poured into ice and the precipitated product was filtered off and recrystallized from methanol, giving 3.14 g of analytically pure product, mp 187°–188° C.

ANALYSIS:

| | | | |
|---|---|---|---|
| Calculated for $C_{15}H_{12}N_4O_2$: | 64.28% C | 4.32% H | 19.99% N |
| Found: | 64.27% C | 4.32% H | 19.73% N |

EXAMPLE 11

6-Ethyl-3-(2-pyridyl)-6H-isoxazolo[5,4-d]pyrazolo[3,4-b]pyridine (1-Ethyl-4-isopropylideneaminooxy-1H-pyrazolo[3,4-b]pyridine-4-yl) (2-pyridyl)carbinol (8.3 g) was dissolved in 150 ml of dichloromethane and to this was added 6.5 g of pyridinium chlorochromate. The reaction mixture was stirred 1 hour and then 300 ml of ether was added, after which the mixture was filtered through a pad of magnesium silicate. The pad was washed with a total of 2 liters of ether and then with 1 liter of 5% methanol/dichloromethane. Concentration of the combined filtrate under a reduced pressure gave 5.8 g of the 1-ethyl-4-hydroxy-5-(2-pyridinyl)-1H-pyrazolo[3,4-b]pyridine, whose identity was confirmed by its mass spectrum.

Some of this ketone (3.3 g) was heated overnight at 100° in 50 ml of pyridine containing 3.0 g of hydroxylamine hydrochloride. At the end of this time the pyridine was evaporated and the residue triturated with 5% hydrochloric acid to give a solid amorphous product, amounting to 1.6 g, mp 146°–147°. This product was combined with the products of several other runs and flushed over a silica gel column with 1:1 ethyl acetate/dichloromethane. Recrystallization of the product obtained in this manner from cyclohexane gave analytically pure material, mp 151°–153° C.

ANALYSIS:

| | | | |
|---|---|---|---|
| Calculated for $C_{14}H_{11}N_5O$: | 63.39% C | 4.18% H | 26.40% N |
| Found: | 63.59% C | 4.31% H | 26.77% N |

EXAMPLE 12

5-Benzoyl-1-ethyl-4-isopropylidenaminooxy-1H-pyrazolo[3,4-b]pyridine

In 25 ml of dry tetrahydrofuran (THF hereafter) was dissolved 1.6 g of acetone oxime, followed by 2.46 of potassium t-butoxide. After stirring 0.5 hour 5.0 g of 5-benzoyl-4-chloro-1-ethyl-1H-pyrazolo[3,4-b]pyridine in 50 ml of THF was added to the solution. After an additional 0.5 hour the reaction was quenched with ammonium chloride solution and the product was extracted with ether. Evaporation of the organic phase and recrystallization of the residue from ethanol gave 4.1 g of product, mp 115°–116° C.

ANALYSIS:

| | | | |
|---|---|---|---|
| Calculated for $C_{18}H_{18}N_4O_2$: | 67.06% C | 5.63% H | 17.38% N |
| Found: | 66.80% C | 5.73% H | 17.29% N |

EXAMPLE 13

5-(4-Chlorobenzoyl)-1-ethyl-4-isopropylidenaminooxy-1H-pyrazolo[3,4-b]pyridine Acetone oxime (1.6 g) was dissolved in 50 ml of THF and potassium t-butoxide (2.46 g) was added. After stirring 30 minutes 6.2 g of 4-chloro-5-(4-chlorobenzoyl)-1-ethyl-1H-pyrazolo[3,4-b]pyridine in 50 ml of THF was added to the solution. After 30 minutes of further stirring, the reaction mixture was distributed between ether and ammonium chloride solution. Drying and evaporation of the organic phase gave a solid which was recrystallized from ethanol to give 4.91 g of product, mp 112°–113° C.

ANALYSIS:

| | | | |
|---|---|---|---|
| Calculated for $C_{18}H_{17}ClN_4O_2$: | 60.59% C | 4.80% H | 15.70% N |
| Found: | 60.75% C | 5.09% H | 15.75% N |

EXAMPLE 14

(1-Ethyl-4-isopropylidenaminooxy-1H-pyrazolo[3,4-b]pyridin-4-yl)(2-pyridyl)carbinol Twenty-five ml of 1.44M n-BuLi was dissolved in 100 ml of anhydrous ether and chilled to −65°. 2-Bromopyridine (5.70 g) was then added dropwise and stirring was continued for 30 minutes. This solution was then added under nitrogen pressure through a catheter to 8.30 g of 1-ethyl-5-formyl-4-isopropylidenaminoxy-1H-pyrazolo[3,4-b]pyridine in 100 ml of THF at ice bath temperature. This reaction mixture was stirred for additional 30 minutes and then distributed between 5% hydrochloric acid and ether. The aqueous phase was washed well with ether and then made basic by pouring it over solid sodium bicarbonate. The product was extracted with dichloromethane and purified by preparative HPLC (5% methanol-dichloromethane, 200 ml/minute) to give 6.20 g of product, mp 131°–133° C. Recrystallization from dichloromethane-hexane raised the mp to 134°–135° C.

ANALYSIS:

| | | | |
|---|---|---|---|
| Calculated for $C_{17}H_{19}N_5O_2$: | 62.75% C | 5.89% H | 21.53% N |
| Found: | 62.52% C | 6.06% H | 21.43% N |

EXAMPLE 15

4-Chloro-1-ethyl-1H-pyrazolo[3,4-b]pyridine-5-carboxaldehyde

Wet $MnO_2$ (110 g) was refluxed for 90 minutes in 1 L of toluene with a Dean-Stark trap for the separation of water. This suspension was then cooled and the 4-chloro-1-ethyl-1H-pyrazolo[3,4-b]pyridine-5-methanol (17.5 g, 82.7 mmole) was added in 50 ml of toluene. The reaction mixture was then stirred for 6 hours and filtered with the aid of a filter pad. The toluene was evaporated and the residue added again to 100 g of wet $MnO_2$ freshly prepared in the above manner. After additional 4 hours the reaction was briefly warmed at 55° and then filtered again through a filter pad. The residue which remained after evaporation of the toluene was purified by preparative high performance liquid chromatography (10% ethyl acetate/hexane, 250 ml/min) to yield 11.70 g of 4-chloro-1-ethyl-1H-pyrazolo[3,4-b]pyridine-5-carboxaldehyde, mp 89°–90° C.

ANALYSIS:

| | | | |
|---|---|---|---|
| Calculated for $C_9H_8ClN_3O$: | 51.56% C | 3.85% H | 20.05% N |
| Found: | 51.18% C | 3.79% H | 19.84% N |

EXAMPLE 16

1-Ethyl-4-isopropylidenaminooxy-1H-pyrazolo[3,4-b]pyridine-5-carboxaldehyde

Potassium t-butoxide (6.70 g) was added to 4.40 g of acetone oxime in 100 ml of dimethylacetamide and the solution stirred for 1 hour. This mixture was then added as a suspension through a catheter to 12.6 g of 4-chloro-1-ethyl-1H-pyrazolo[3,4-b]pyridine-5-carboxaldehyde in 200 ml of THF, chilled with ice/water.

After stirring for additional 30 minutes the reaction was quenched with ammonium chloride solution and then distributed between dichloromethane and water. The organic phase was dried, evaporated and chromatographed (20% ethyl acetate/hexane, 200 ml/min) to give, after combination of the appropriate fractions, 10.15 g of product, mp 85°–87° C.

ANALYSIS:

| | | | |
|---|---|---|---|
| Calculated for $C_{12}H_{14}N_4O_2$: | 58.52% C | 5.73% H | 22.75% N |
| Found: | 58.55% C | 5.60% H | 22.83% N |

I claim:
1. A compound having the formula

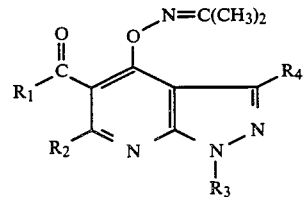

where $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl, the term aryl in each occurrence signifying an unsubstituted phenyl group or a phenyl group substituted with 1, 2 or 3 substituents each of which being independently a loweralkyl group, loweralkoxy group, hydroxy group, trifluoromethyl group, chlorine or fluorine, with the proviso that the aryl group shall not have chlorine or fluorine at the ortho position; the term heteroaryl in each occurence signifying a group having the formula

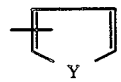

where Y is O, S, $NR_6$ or $CH=N$, $R_6$ being hydrogen, loweralkyl or phenylloweralkyl; and the term cycloalkyl signifying a cycloalkyl group of 3 to 7 carbon atoms.

2. The compound as defined in claim 1, wherein $R_1$ is aryl or heteroaryl.

3. The compound as defined in claim 1, where $R_2$ is hydrogen.

4. The compound as defined in claim 1, where $R_3$ is loweralkyl.

5. The compound as defined in claim 1, where $R_4$ is hydrogen.

6. The compound as defined in claim 1, which is 1-ethyl-4-isopropylidenaminooxy-1H-pyrazolo[3,4-b]pyridine-5-carboxaldehyde.

7. A compond having the formula

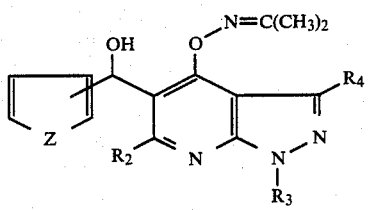

where Z is O, S, $NR_5$ or CH=N, $R_5$ being loweralkyl, phenylloweralkyl or benzenesulfonyl; $R_2$ is hydrogen or loweralkyl; $R_3$ is loweralkyl; loweralkoxyloweralkyl, cycloalkyl, arylloweralkyl or heteroarylmethyl; and $R_4$ is hydrogen or loweralkyl, the term heteroaryl signifying a group having the formula

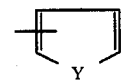

where Y is O, S, $NR_6$ or CH=N, $R_6$ being hydrogen, loweralkyl or phenylloweralkyl; and the term cycloalkyl signifying a cycloalkyl group of 3 to 7 carbon atoms.

8. The compound as defined in claim 2, which is 5-benzoyl-1-ethyl-4-isopropylidenaminooxy-1-H-pyrazolo[3,4-b]pyridine.

9. The compound as defined in claim 2, which is 5-(4-chlorobenzoyl)-1-ethyl-4-isopropylidenaminooxy-1H-pyrazolo[3,4-b]pyridine.

10. The compound as defined in claim 7, where Z is CH=N.

11. The compound as defined in claim 7, where $R_2$ is hydrogen.

12. The compound as defined in claim 7, where $R_3$ is loweralkyl.

13. The compound as defined in claim 7, where $R_4$ is hydrogen.

14. The compound as defined in claim 10, which is (1-ethyl-4-isopropylidenaminooxy-1H-pyrazolo[3,4-b]pyridin-4-yl)(2-pyridyl)carbinol.

* * * * *